(12) United States Patent
Zylka et al.

(10) Patent No.: US 6,379,043 B1
(45) Date of Patent: Apr. 30, 2002

(54) X-RAY EXAMINATION APPARATUS AND METHOD FOR GENERATING DISTORTION-FREE X-RAY IMAGES

(75) Inventors: Waldermar Zylka, Hamburg; Jörg Sabczynski, Norderstedt; Jürgen Weese, Henstedt-Ulzburg, all of (DE)

(73) Assignee: U.S. Philips Corporation, New York, NY (US)

(*) Notice: Subject to any disclaimer, the term of this patent is extended or adjusted under 35 U.S.C. 154(b) by 0 days.

(21) Appl. No.: 09/601,825

(22) PCT Filed: Jun. 15, 2000

(86) PCT No.: PCT/EP99/09455

§ 371 Date: Aug. 8, 2000

§ 102(e) Date: Aug. 8, 2000

(87) PCT Pub. No.: WO00/33740

PCT Pub. Date: Jun. 15, 2000

(51) Int. Cl.[7] .............................................. G01D 18/00
(52) U.S. Cl. ....................................... 378/207; 378/164
(58) Field of Search ................................. 378/207, 162, 378/164, 205

(56) References Cited

U.S. PATENT DOCUMENTS 5,748,768 A * 5/1998 Sivers et al. ................. 382/130
5,772,594 A 6/1998 Barrick ........................ 600/407

FOREIGN PATENT DOCUMENTS

| DE | 197 03 556 A1 | * 8/1998 |
| EP | 0 623 884 A2 | * 11/1994 |
| FR | 2 631 810 | * 12/1989 |

* cited by examiner

Primary Examiner—David P. Porta
(74) Attorney, Agent, or Firm—John Vodopia

(57) ABSTRACT

The invention relates to an X-ray examination apparatus for and a method of forming distortion-free X-ray images, which apparatus and method enable the imaging properties of the C-arm X-ray system to be derived from the patient image. To this end, a reference image (FIG. 4) is formed in a reference orientation of the X-ray examination apparatus and the reference imaging properties of the C-arm X-ray system are determined on the basis of the positions of calibration members (7, 8), which are mounted on the image intensifier (2) and/or the X-ray source (3) and are reproduced, and the known geometry and position relative to the image intensifier (2) and/or the X-ray source (3); the positions of the calibration members (7, 8) reproduced in a patient X-ray image (FIG. 5) are compared with the positions of the calibration members (7, 8) in the reference image (FIG. 4) and distortions occurring in the patient X-ray image are corrected on the basis of differences between the reproduced positions of the calibration members (7, 8) in the patient X-ray image (FIG. 5) and in the reference image (FIG. 4).

9 Claims, 2 Drawing Sheets

X-RAY EXAMINATION APPARATUS AND METHOD FOR GENERATING DISTORTION-FREE X-RAY IMAGES

BACKGROUND OF THE INVENTION

The invention relates to an X-ray examination apparatus for and a method of forming distortion-free X-ray images.

Such X-ray examination apparatus and methods for forming distortion-free X-ray images are used for given surgical interventions, notably in orthopedics, for example, in order to observe the position of organs and bones of the patient. Mobile X-ray examination apparatus such as, for example, C-arm X-ray systems, are moved to a position near the operating table as required. Because of the mobile components of such an X-ray examination system and the continuously changing exposure circumstances, the X-ray images must be checked regularly for distortions. Methods and devices of this kind are also used for computer-aided surgery.

U.S. Pat. No. 5,772,594 describes a C-arm X-ray system in which a plurality of reference sensors are mounted on the image intensifier, said reference sensors being localized by a position measuring system. The bone to be treated is provided with markers which are localized by said position measuring system. In this X-ray system the image formed is displayed by means of an image processing device and the surgical tools of the surgeon, also being provided with sensors, are localized by the position measuring system and reproduced in the displayed X-ray image of the relevant bone. Changes of the position of the bone which occur during the intervention and after the formation of the image are not reproduced.

Images produced by X-ray examination apparatus are usually distorted. Such distortions are due on the one hand to the curved surface of the image intensifier and on the other hand to changes of the external magnetic field. Moreover, notably C-arm X-ray examination apparatus are subject to bending due to the weight of the image intensifier and the X-ray source, said bending not being constant. Such bending and distortions lead to changes in the imaging properties and hence to X-ray images containing defects. Mobile C-arms can be moved to a different position or into a different orientation by the surgeon at any time, so that the imaging properties change continuously.

For novel surgical techniques such as CAS (Computer-Aided Surgery) it is necessary to know the imaging properties of the X-ray examination apparatus completely.

Therefore, it is an object of the invention to provide a method and a device which enable determination of the imaging properties of the X-ray examination apparatus from the patient images.

This object is achieved according to the invention in that the X-ray examination apparatus includes at least one calibration member which is arranged in the X-ray beam path and is reproduced in a reference image, and a correction unit which is arranged to correct distortions in X-ray images by calculating imaging properties of the X-ray examination apparatus on the basis of differences between the positions of the reproductions of the calibration members in a patient X-ray image and in the reference image.

SUMMARY OF THE INVENTION

The calibration members are mounted on the housing of the X-ray source and/or on the housing of the image intensifier and hence are reproduced in each X-ray image. A reference image is formed in a reference orientation. The positions of the calibration members reproduced in the reference image are determined and stored. The imaging properties of the X-ray examination apparatus are determined by means of the known geometry of the calibration members and the known position and orientation relative to the image intensifier and the X-ray source.

In comparison with the formation of the reference image, during the formation of the patient X-ray image the X-ray examination apparatus may have a different orientation or other effects falsifying the patient X-ray image may occur. The correction unit compares the positions of the reproductions of the calibration members in the patient image with the stored positions of the calibration members in the reference image. Distortions in the patient X-ray image are calculated and corrected on the basis of the resultant differences between positions of the calibration members in the patient image and the positions in the reference image, so that the output unit delivers a distortion-free X-ray image.

The imaging properties of X-ray examination apparatus can be determined by means of reference images of objects of known geometry, that is, so-called calibration members. When these imaging properties of the X-ray examination apparatus are known, images of other objects, for example patient X-ray images, can be corrected.

The reference image is applied to an arithmetic unit. The arithmetic unit calculates the reference imaging properties from the positions of the reproductions of the calibration members in said reference image and the known dimensions of the X-ray examination apparatus; these reference imaging properties are stored in a memory.

In a further embodiment of the invention reference markers are provided on the image intensifier and/or the X-ray source. These reference markers are localized by a position measuring device. The position measuring device defines a system of co-ordinates in which the positions of the reference markers are measured. The measured positions are applied to the arithmetic unit. The reference imaging properties of the X-ray examination apparatus are determined on the basis of the distances between reference markers and calibration members on the image intensifier and the X-ray source and the known geometry relative to the reference markers.

A calibration phantom, which may have a shape other than that of the calibration members, is introduced into the X-ray beam path, for example on the patient or on the operating table. Reference markers are provided on this calibration phantom. These reference markers are also measured by the position measuring device so as to be applied to the arithmetic unit. The position of the calibration phantom in the system of co-ordinates is determined on the basis of the known geometrical shape of the calibration phantom and the positions of the reference markers. The position of the calibration phantom in the patient X-ray image to be formed is calculated on the basis of the known position of the calibration phantom in the system of co-ordinates and the previously calculated reference imaging properties. The calculated position of the calibration phantom is compared with the actual position of the calibration phantom in the patient X-ray image. The imaging properties of the X-ray examination apparatus during the formation of the patient X-ray image are calculated on the basis of the differences occurring and distortions in the patient X-ray image are corrected, if necessary, in the correction unit.

It has been found that it is advantageous to arrange the calibration members in a circular pattern in a disc which is transparent to X-rays. This enables the calibration members to be reproduced at the edge of the patient X-ray image, so that the X-ray image is affected as little as possible. The calibration members preferably consist of metal spheres which absorb the X-rays and hence are visible in the X-ray image.

The calibration members in a further embodiment are provided in the form of as crossed metal wires in a transparent disc. A free zone without calibration members is thus created again in the focus of the X-ray beam path. Moreover, on the basis of the crossed metal wires distortions can already be detected by the naked eye, because the normally straight metal wires are bent in the reference image in the case of distortions in the patient X-ray image.

It has been found that from a construction point of view it is advantageous to mount calibration phantoms, provided with reference markers, directly on the patient or on the operating table. The position of the reference markers can be localized by the position measuring device. In the different orientations of the X-ray examination apparatus it may occur that some reference markers are masked, so that they cannot be localized by the position measuring device. In that case it is advantageous to take recourse to calibration members or phantoms whose reference markers can be localized by the position measuring device.

The object according to the invention is also achieved by means of a method of forming distortion-free X-ray images wherein an X-ray examination apparatus which includes an X-ray source, an image intensifier and calibration members forms reference images in reference orientations of the X-ray examination apparatus with calibration members which are mounted on the image intensifier or the X-ray source and are reproduced, the positions of the calibration members reproduced in a patient X-ray image being compared with the positions of the calibration members in the corresponding reference image and distortions occurring in the X-ray image which are due to differences being corrected.

According to a further version of the invention a plurality of reference images are formed, the respective reference imaging properties being determined for each of these reference images. For the comparison of the positions of the calibration members in the patient X-ray images, that reference image is selected whose orientation best resembles the orientation of the X-ray examination apparatus during the acquisition of the patient X-ray images. The positions of the calibration members in this appropriate reference image are compared with the positions of the calibration members in the patient X-ray image; the imaging properties are calculated and any distortions in the rendition of the patient X-ray image are corrected on the basis of resultant differences.

It has been found that it is advantageous to acquire a plurality of reference images in different orientations. For these different orientations the respective reference imaging properties are calculated and stored in a memory. The orientation-dependent reference imaging properties are stored in a look-up table and are composed of a plurality of relevant data, for example, the position of the X-ray source relative to the image intensifier and the position of the X-ray examination apparatus relative to an external reference member, for example the patient. The reference imaging properties can thus be calculated for all feasible orientations of the X-ray examination apparatus by interpolation. For the comparison of the positions of the calibration members, the data in the look-up table are used as a reference; this data is then compared with the actual positions of the reproduction of the calibration members in the patient X-ray image. Distortions in the patient X-ray image are corrected on the basis of the resultant differences. This version enhances the accuracy of the calculation of the imaging properties, because it is possible to imitate any orientation of the X-ray examination apparatus during the acquisition of the patient X-ray image.

The X-ray examination apparatus and the method according to the invention enable the removal of distortions in the patient X-ray images by means of a previously formed reference image and imaging properties determined therefrom. The patient to be examined is not exposed to an additional X-ray dose. For the removal of distortions from the acquired X-ray images it is necessary to know the imaging properties, particularly in the case of mobile X-ray examination apparatus in which the exposure circumstances often change significantly.

In the field of surgical navigation it is also possible to reproduce the position and orientation of surgical tools in the distortion-free patient X-ray images when the imaging properties of the X-ray examination apparatus are known.

Preferably, a C-arm X-ray apparatus is used as the X-ray examination apparatus. An X-ray examination apparatus and method in accordance with the invention are in principle also suitable for use in the fields of tomosynthesis and computer tomography, because for such applications the imaging properties of the relevant X-ray apparatus must also be accurately known for the reconstruction of patient X-ray images or the removal of distortions therefrom.

BRIEF DESCRIPTION OF THE DRAWINGS

An embodiment according to the invention will be described in detail hereinafter with reference to the drawing. Therein.

DESCRIPTION OF THE PREFERRED EMBODIMENTS

Figure 1:
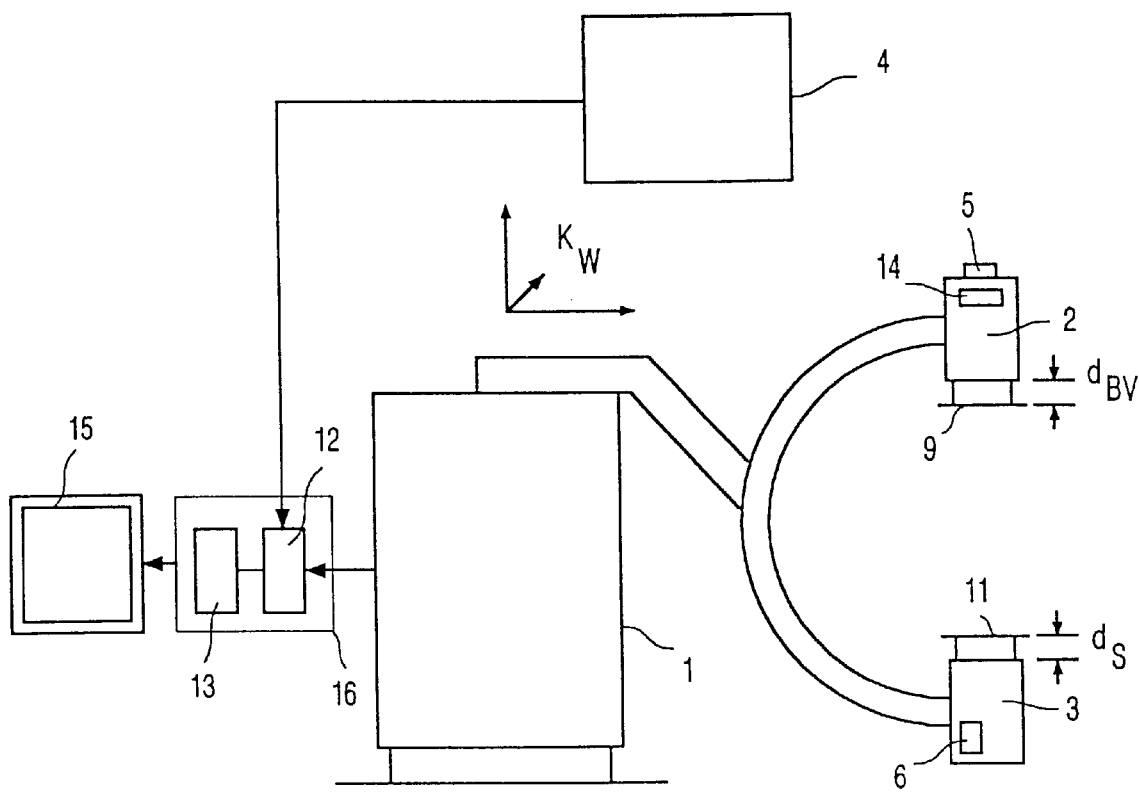
FIG. 1 shows diagrammatically a C-arm X-ray system.

FIG. 1 shows an image intensifier 2 and an X-ray source 3 which are mounted on the housing 1 of a C-arm X-ray device. On the image intensifier 2 calibration members 8 are provided in a disc 9 at a distance $d_{By}$. The image intensifier 2 includes a CCD camera 14 whereby the patient X-ray image is acquired and applied to the image processing unit 16. Reference markers 5 are provided on the image intensifier 2. These reference markers 5 may be realized by means of LEDs in the case of optical position measuring devices 4; however, they may alternatively consist of simple geometrical members having unambiguous shapes which can be localized and distinguished by a position measuring device 4. In the case of magnetic position measuring devices, such reference markers may be formed as magnetic sensors. Position measuring devices based on radio or infrared transmission can also be used.

Opposite the image intensifier 2 there is arranged the X-ray source 3 which emits the X-rays which are subsequently picked up by the image intensifier in which this radiation is converted into visible light which is picked up by the CCD camera 14 and transported to the image processing system 16. The X-ray source 3 is also provided with reference markers 6 which are localized by the position measuring device 4. A transparent disc 11 with the calibration members 7 in the form of crossed metal wires is arranged in front of and at a distance $d_s$ from the X-ray source 3. The image processing unit 16 includes an arithmetic unit 12 and a correction unit 13. The output unit 15 outputs the patient X-ray image wherefrom distortions have been removed.

A reference image is formed in which the calibration members 7, 8 are reproduced. The reference image with the reproduced calibration members can be acquired already after the manufacture of the X-ray examination apparatus as well as directly prior to the surgical intervention. It is applied to the arithmetic unit 12. The arithmetic unit 12 determines the positions of the calibration members in the reference image and calculates the reference imaging properties on the basis of the known geometry of the C-arm X-ray apparatus. These reference imaging properties are stored in a memory which is not shown.

Additionally, the positions of the image intensifier 2 and of the X-ray source 3 in a space system of co-ordinates $K_w$ become known by the localizing of the reference markers 5 and 6 by the position measuring device 4.

Figure 4:
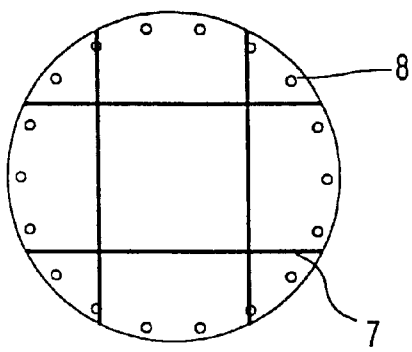
FIG. 4 shows the reference image with calibration members.
Figure 5:
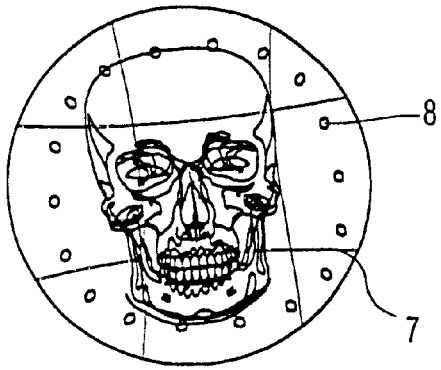
FIG. 5 shows a distorted patient X-ray image.

The arithmetic unit 12 compares the stored positions of the calibration members 7 and 8 in the form of the crossed wires 7 and the metal spheres 8 in a circular array, as derived from the reference image (FIG. 4), with the positions of the reproductions of the calibration members in the patient X-ray image (FIG. 5).

Figure 6:
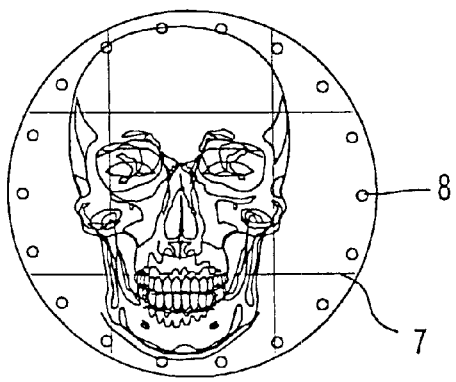
FIG. 6 shows a patient X-ray image wherefrom distortions have been removed.

After formation of the patient X-ray image in a different orientation of the C-arm, a distorted patient X-ray image could occur (FIG. 5). Such distortions in the patient X-ray image cause differences between the positions of the calibration members. Using these differences and the reference imaging properties, the changes of the imaging properties are calculated for the C-arm X-ray system. The correction of distortions in the patient X-ray image is performed in the correction unit 13 on the basis of this calculation. The patient X-ray image wherefrom distortions have been removed (FIG. 6) is displayed, for example on a monitor by means of the output unit 15.

Figures 2, 3:
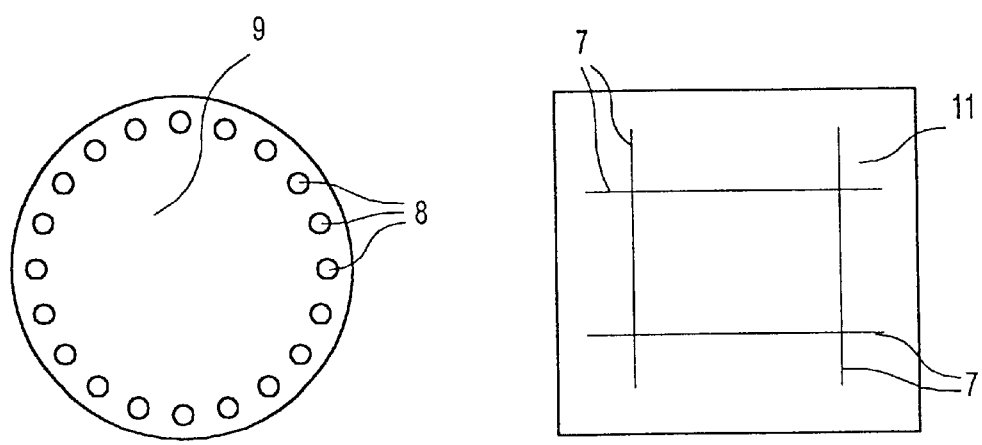
FIG. 2 shows calibration members of the image intensifier.
FIG. 3 shows calibration members on the X-ray source.

The FIGS. 2 and 3 show the discs 9 and 11 in which the calibration members 7 and 8, respectively, are provided. All calibration members are arranged at the edge of the disc so as to ensure that the field for the imaging of the patient, and hence the observation of the patient X-ray image by the surgeon, is affected as little as possible.

The calculation of the differences between the positions of the calibration members in the patient X-ray images and those in the reference images will be briefly described hereinafter. It is assumed that p is an arbitrary parameter of the model describing the imaging properties of the C-arm X-ray system. Let $B_R$ be the reference image, $B_p$ the patient image, and $K(B)=\{k_i(B)\}$ the set of all positions of the calibration members $k_i(B)$ in the image B. The estimated value of the parameter $\bar{p}$ is a function of K(B). $\bar{p}$ can thus be developed in a Taylor's series in conformity with the differences between the position of the calibration members in the patient image and in the reference image:

$$\bar{p}(K(B_p))=\bar{p}(K(B_R))+c_1(K(B_p)-K(B_R))+c_2(K(B_p)-K(B_R))^2+.$$

This equation is shown in simplified form and the actual equation is more complex. The constants c1, C2 . . . result from the imaging model. Some parameters of the imaging model do not or change or change only insignificantly and can be measured with the reference image and taken over for the patient image without modification. The parameters that are concerned in this respect are dependent on the relevant C-arm X-ray system and can be determined either by measurements or by model calculations. For example, the bending of the C-arm X-ray system also implies a change of the relative orientation (rotation) of the image intensifier with respect to the X-ray source. This effect, however, can usually be ignored in comparison with the change of the relative position (translation) of the two housings with respect to one another. A few calibration members in the patient image already suffice to determine the three parameters of the translation. The number of calibration members in the patient image may thus be significantly smaller than the number of calibration members required in the reference image so as to determine all parameters of the imaging model.

The amount of calculation work required can be reduced by way of a plurality of reference images and associated calculated reference imaging properties. Because the patient X-ray image is usually acquired in an orientation other than that in which the reference image is acquired, the number of parameters to be calculated can be reduced by using reference images acquired in typical, frequently occurring orientations; the reference image whose orientation is most similar to the orientation of the patient X-ray image can then be selected for the calculation of the imaging properties.

A calibration phantom (not shown) is provided with reference markers, is introduced into the X-ray beam path and attached, for example to the patient or to the operating table. Because it is provided with reference markers in exactly the same way as the image intensifier and the X-ray source, it can be localized by the position measuring device. Its positions and dimensions can thus be defined in the system of co-ordinates. The position of the calibration phantom is calculated for the patient X-ray image and compared with the positions and reproductions of the calibration phantom in the actual patient X-ray image. The imaging properties of the C-arm can thus also be determined.

The calibration phantom may also be a surgical tool provided with reference markers. In that case it can be reproduced on the monitor with the corrected imaging properties, without a further X-ray image being required.

A three-dimensional X-ray image is reconstructed from a plurality of slice images in the case of computed tomography (CT). Because external magnetic fields also act on the CT apparatus and shifts between the X-ray source and the detector have a negative effect on the patient X-ray image, the reconstruction of a distortion-free free X-ray image requires knowledge of the imaging properties of the CT apparatus. The calibration members are in this case arranged in such a manner that they are visible in each slice image; the imaging properties of the CT apparatus can be determined on the basis of the differences between the positions of the calibration members reproduced in the reference image and the positions of the calibration members reproduced in the patient X-ray image.

In the case of tomosynthesis, also involving the acquisition of slice images, distortions can be corrected according to the invention by utilizing calibration members and determining the imaging properties.

What is claimed is:

1. An X-ray examination apparatus comprising:
   at least one calibration member which is arranged in the X-ray beam path and is reproduced in a reference image, at least one reference marker which is mounted on an image intensifier and/or an X-ray source, and also a calibration phantom which is provided with further reference markers and is arranged in the X-ray beam path, and a correction unit which is arranged to correct distortions in X-ray images by calculating imaging properties of the X-ray examination apparatus on the basis of differences between the positions of the reproductions of the calibration members in a patient X-ray image and in the reference image.

2. An X-ray examination apparatus as claimed in claim 1, further comprising:

an arithmetic unit for calculating reference imaging properties from known dimensions of the X-ray examination apparatus and the positions of the calibration members in the reference image acquired in a reference orientation, and a display unit for displaying the distortion-free X-ray image.

3. An X-ray examination apparatus as claimed in claim 1, further comprising:

a position measuring device for measuring the positions of the reference markers in a fixed co-ordinate system K, formed by the position measuring device and the arithmetic unit for supplying the measured positions.

4. An X-ray examination apparatus as claimed in the claim 1, further comprising a memory for the storage of a plurality of reference imaging properties.

5. An X-ray examination apparatus as claimed in the claim 1, further comprising at least one calibration member provided in a disc which is arranged in the X-ray beam path and which is transparent to X-rays.

6. An X-ray examination apparatus as claimed in the claim 1, wherein said at least one calibration member includes X-ray absorbing members.

7. A method of forming a distortion-free X-ray image by means of an X-ray examination apparatus which includes an X-ray source, an image intensifier and calibration members, comprising the steps of:

mounting at least one reference marker on the image intensifier and/or the X-ray source, arranging a calibration phantom having further reference markers in the X-ray beam path, forming reference images in reference orientations of the X-ray examination apparatus with calibration members which are mounted on the image intensifier or the X-ray source and are reproduced, reproducing the positions of the calibration members in a patient X-ray image, comparing the positions of the calibration members in the patient X-ray image with the positions of the calibration members in the corresponding reference image, and correcting distortions occurring in the X-ray image.

8. A method of forming a distortion-free X-ray image as claimed in claim 7, wherein from a plurality of reference images formed in different orientations and from reference imaging properties calculated therefrom that reference image is selected whose orientation is most similar to the orientation of the X-ray examination apparatus during the acquisition of the patient X-ray image in order to compare the positions of the calibration members in the patient X-ray image and in the selected reference image so as to calculate imaging properties on the basis thereof and to carry out, if necessary, corrections in the patient X-ray image.

9. A method of forming a distortion free X-ray image as claimed in the claim 7, wherein reference imaging properties are calculated from reference images formed in a plurality of orientations, which properties are calculated, by way of interpolation, for all feasible orientations of the examination apparatus and are stored in a look-up table.

* * * * *